United States Patent [19]
McCarty

[11] Patent Number: 5,107,709
[45] Date of Patent: Apr. 28, 1992

[54] ULTRASONIC BEAM AIMING APPARATUS AND METHOD FOR NONDESTRUCTIVE TESTING

[75] Inventor: John R. McCarty, Akron, Ohio

[73] Assignee: Bridgestone/Firestone, Inc., Akron, Ohio

[21] Appl. No.: 503,003

[22] Filed: Apr. 2, 1990

[51] Int. Cl.$^5$ .............................................. G01D 5/32
[52] U.S. Cl. ................................................... 73/655
[58] Field of Search ............. 73/601, 620, 627, 653, 73/655, 628, 644; 128/661.06, 663.01

[56] References Cited

U.S. PATENT DOCUMENTS

| | | | |
|---|---|---|---|
| 3,063,290 | 11/1962 | Kaserman et al. | 73/622 |
| 3,213,677 | 10/1965 | Maklary | 73/615 |
| 3,371,660 | 3/1968 | Carlin | 128/661.06 |
| 3,728,027 | 4/1973 | Watanabe | 356/13 |
| 3,861,806 | 1/1975 | Born | 356/152 |
| 4,274,289 | 6/1981 | Weiss et al. | 73/618 |
| 4,484,569 | 11/1984 | Driller et al. | 128/661.06 |
| 4,554,834 | 11/1985 | Prinz et al. | 73/644 |
| 4,760,304 | 7/1988 | Oliver | 73/628 |

Primary Examiner—Hexron E. Williams
Assistant Examiner—Louis M. Arana
Attorney, Agent, or Firm—Ernst H. Ruf

[57] ABSTRACT

The accurate positioning of an ultrasonic beam (21) to nondestructively test an object (11) is achieved by an ultrasonic beam aiming apparatus (10) including an ultrasonic transducer (20) generating an ultrasonic beam (21) having a focal point (22) and axis (23), and a point-source lamp (30) and mirror (31) generating a visible light beam (32) having a focal point (33) and axis (34). The visible light beam focal point (33) is selectively coaxially movable into and out of coincident at points exterior and interior to the object (11). The location of the ultrasonic beam focal point (22) may be found by aligning the ultrasonic beam focal point (22) and the visible light beam focal point (33) to coincide at an alignment spot, and moving the aligned ultrasonic beam focal point (22) to a point of interest within the object while maintaining the visible light beam focal point (33) at the alignment spot.

13 Claims, 1 Drawing Sheet

ULTRASONIC BEAM AIMING APPARATUS AND METHOD FOR NONDESTRUCTIVE TESTING

TECHNICAL FIELD

The present invention relates generally to the nondestructive testing of objects. More particularly, the present invention relates to the use of ultrasonics to nondestructively inspect objects. More specifically, the present invention relates to an apparatus and method for accurately aiming the ultrasonic beam utilized to nondestructively inspect or examine objects internally.

BACKGROUND ART

It has long been known that ultrasonics may be used to provide an accurate indication of various physical properties of a wide variety of objects including the human eye, tubing and pneumatic tires without destruction of the object.

In one exemplary technique, known as quantitative section analysis, dimensional characteristics of an object are found by generating an image of a section of the object along a designated inspection line using an ultrasonic beam. If such an analysis is to be most meaningful, the location of the ultrasonic beam must be accurately located relative to the geometry of the object under test.

A spectrum of techniques have been used in an effort to identify the location of the invisible ultrasonic beam, generally without great accuracy and precision, and with substantial expense and complexity.

It has been recognized that, at least when examining the human eye, visible light is a desirable medium to aim and thereby locate an ultrasonic beam. In U.S. Pat. No. 3,371,660, ultrasonic waves utilized for eye examinations are introduced to the eye coaxially with light directed through a conventional ophthalmoscope. By viewing the eye and a light marker thereon through the ophthalmoscope, the operator can identify the location of ultrasonic waves incident on the eye exterior. However, because the focal points of both the ultrasonic waves and light beam are coincident, any attempt to focus the ultrasonic beam inside the eye will result in a loss of aiming beam sharpness. In this case the operator cannot accurately determine the location inside the eye of the ultrasonic beam.

SUMMARY OF THE INVENTION

It is, therefore, an object of the present invention to provide an apparatus and method for accurate and precise positioning of the focal point of an ultrasonic beam inside an object.

It is another object of the present invention to provide an apparatus and method, as above, in which determining such positioning is economical and straightforward.

It is still another object of the present invention to provide an apparatus and method, as above, which utilizes a visible light based aiming system whose accuracy and precision is not reduced when the ultrasonic beam is focused inside the object.

These and other objects and advantages of the present invention over existing prior art forms will become more apparent and fully understood from the following description in conjunction with the accompanying drawings.

In general, an apparatus for the accurate positioning of an ultrasonic beam to nondestructively test an object includes ultrasonic transducer means for generating the ultrasonic beam and impinging the beam upon the object, the ultrasonic beam having a focal point and a beam axis, and aiming means for generating a visible light beam having a focal point and a beam axis, the visible light beam coaxial with the ultrasonic beam axis and the ultrasonic beam focal point. The visible light beam focal point is selectively coaxially movable into and out of coincidence at points exterior and interior to the object.

A method for the accurate positioning of an ultrasonic beam to nondestructively test an object, includes the steps of generating an ultrasonic beam having a beam axis and having a focal point, and impinging the ultrasonic beam upon the object, generating a visible light beam having a beam axis coaxial with the ultrasonic beam axis and having a focal point, and impinging the visible light beam upon the object, aligning the ultrasonic beam focal point and the visible light beam focal point to coincide at an alignment spot, and, moving the aligned ultrasonic beam focal point to a point of interest within the object.

BRIEF DESCRIPTION OF THE DRAWINGS

FIG. 1 depicts a partial elevation of a test object having an internal area of interest for nondestructive examination.

PREFERRED EMBODIMENT FOR CARRYING OUT THE INVENTION

Figure 1:
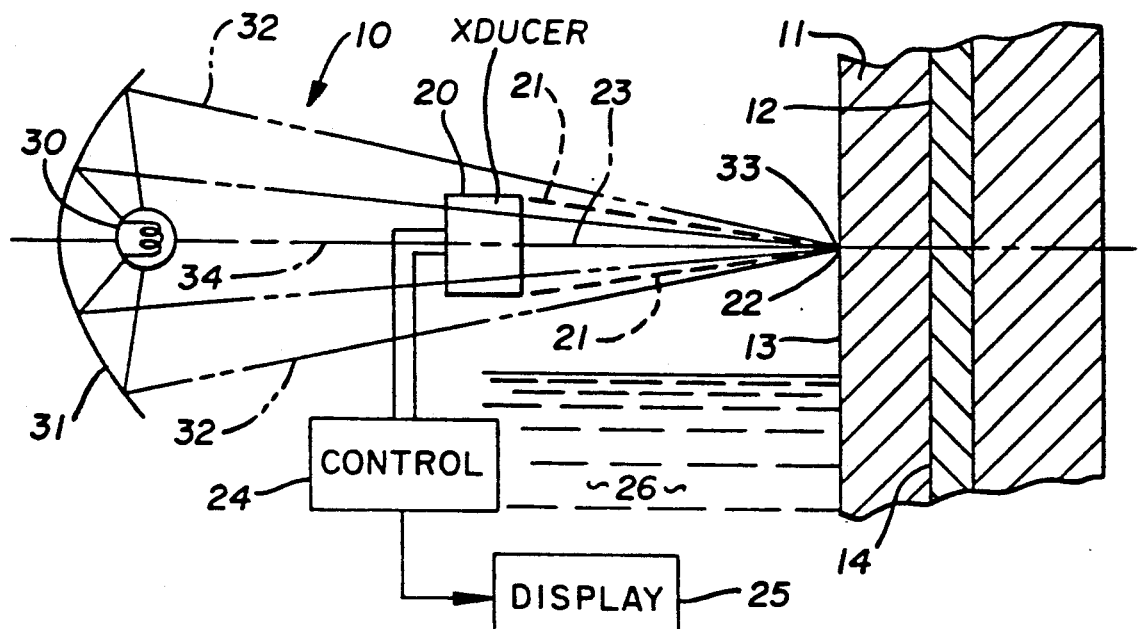
FIG. 1 is an elevational view of an exemplary ultrasonic beam aiming apparatus in accordance with the concept of the present invention for use in a nondestructive object testing system employing fluid-coupled ultrasonics.

FIG. 1 is an elevational view of an exemplary ultrasonic beam aiming apparatus, generally indicated by the reference numeral 10, for use in a testing system employing ultrasonics to nondestructively examine an object 11. The object 11 depicted in partial elevation in FIG. 1 has an internal area 12 of interest for nondestructive examination.

Ultrasonic beam aiming apparatus 10 includes an ultrasonic transducer 20 that generates a beam of ultrasonic energy 21 having a focal point 22 along an ultrasonic beam axis 23 through ultrasonic transducer 20 and ultrasonic beam focal point 22. Ultrasonic transducer 20 may be operated by a conventional ultrasonic generator control 24 and the ultrasonic energy reflected from object 11 presented in a display 25 such as a conventional A scan plot of amplitude versus time. Reflected ultrasonic energy may also be directed to other data collection, analysis or output devices such as a recorder, computer or plotter (not shown).

As is known in the art, ultrasonic beam 21 may be coupled advantageously to object 11 by a suitable liquid such as water. In the exemplary embodiment, the aiming apparatus 10, the ultrasonic transducer 20, and at least a portion of the object 11 are immersed in a suitable liquid such as water.

The ultrasonic beam aiming apparatus 10 embodiment shown in FIG. 1 further includes a source of visible light such as high-intensity point-source lamp 30 connected to a source of suitable power (not shown) and a reflector such as mirror 31 spatially fixed relative to lamp 30 for redirecting and focusing the visible light beam 32 from lamp 30 to a visible light beam focal point 33 along visible light beam axis 34 coaxial with ultrasonic beam focal point axis 23. By generating visible light beam 32 from a location behind ultrasonic transducer 20, the locus of points at which the focal points of the ultrasonic beam 21 and visual light beam 32 both fall are coaxial.

Operation of ultrasonic beam alignment apparatus 20 is straightforward. First, the spatial relationship of lamp 30 and its mirror 31 with that of ultrasonic transducer 20 is adjusted so that visible light beam focal point 33 and ultrasonic beam focal point 22 coincide at the intersection of ultrasonic beam axis 23 and the outside surface 13 of object 11 at the desired entry point (also called the alignment spot). This is preferably accomplished by moving lamp 30 and mirror 31 so that the focal point 33 of visible light beam 32 (whose focal length is fixed) is at the intersection of ultrasonic beam axis 23 and the outside surface 13 of object 11. Thereafter ultrasonic transducer 20 is moved s that the focal point 22 of ultrasonic beam 21 is coincident with visible light beam focal point 33, and ultrasonic beam axis 23 and visible light beam axis 34 are coaxial.

Figure 2:
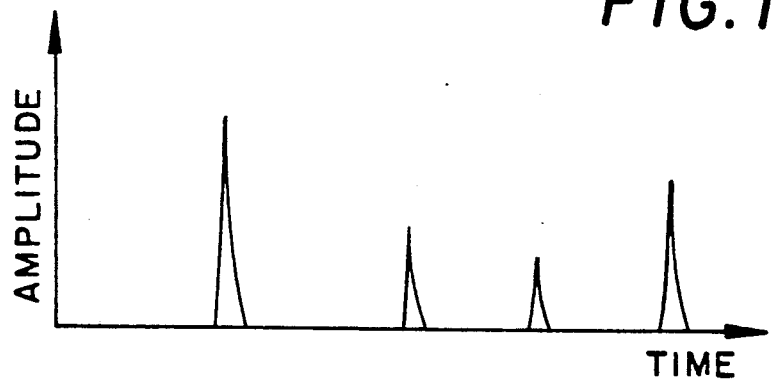
FIG. 2 is an A scan display of the amplitude of the ultrasonic energy reflected over time by the test object depicted in FIG. 1.

Next, ultrasonic beam 21 is focused at the interior boundary of interest while visible light beam focal point 33 remains fixed on surface 13. Since focusing ultrasonic beam 21 at a boundary will maximize the reflected energy from that boundary, ultrasonic beam 21 may be focused at the boundary of interest by moving ultrasonic transducer 20 axially (by means not relevant herein) until the appropriate echo pulse on the A scan display shown in FIG. 2 is of maximum amplitude.

Figure 3:
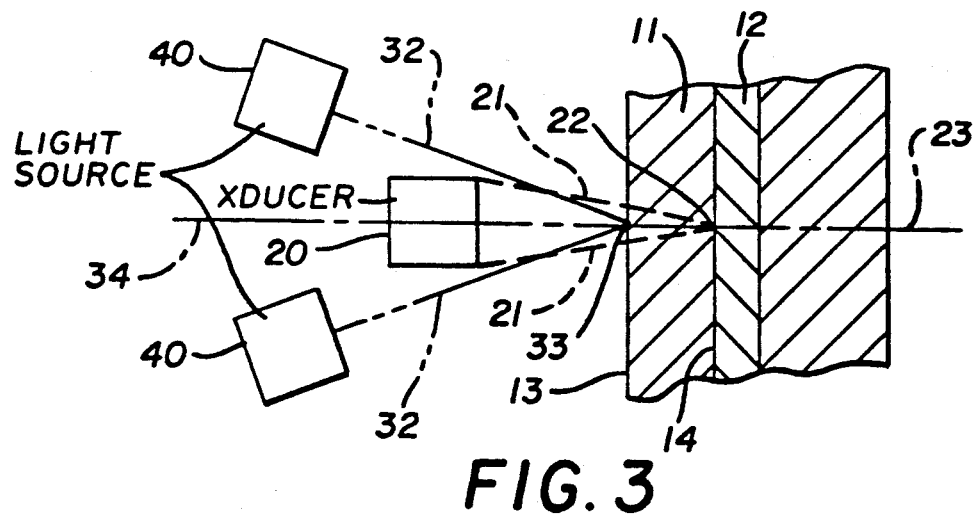
FIG. 3 is an elevational view of an alternative exemplary ultrasonic beam aiming apparatus in accordance with the concept of the present invention including a plurality of visible light beam generators focusable at the same point along the axis of the ultrasonic beam focal point.

Here, solely for explanatory purposes it shall be assumed that the interior boundary of interest is the boundary of internal area 12, designated with the number 14 in FIGS. 1 and 3. In this case the second pulse in FIG. 2 represents the reflection of boundary 14.

Once coincidence of the ultrasonic beam focal point 22 and visible light beam focal point 33 has been established, the position of ultrasonic beam focal point 22 may be varied within object 11 and will be located along the axis identified by visible light beam 32. So long as visible light beam focal point 33 is maintained at surface 13, its intersection point with surface 13 will provide a readily visible accurate and precise indication of the axial position of ultrasonic beam focal point 22 within object 11.

The skilled artisan will appreciate that other techniques exist for aligning ultrasonic beam focal point 22 and visible light beam focal point 33 and are within the scope of the present invention.

The skilled artisan will further appreciate that components may be varied and will still be within the scope of the present invention. For example, FIG. 3 presents an alternative embodiment of ultrasonic beam aiming assembly 10 in which a plurality of smaller, point light sources or fiber optic cable fixtures 40 may be fixedly mounted in spaced quadrature relation to each other (by means not relevant herein) and in a position so that the visible aiming light they provide converge at the visible light beam focal point 33. Thus, it should be understood that the scope of the present invention includes any visible light source and aiming scheme where visible light beam 32 converges at visible light beam focal point 33. Also, the specific transducer selected as ultrasonic transducer 20 may be varied so that its characteristics (such as focal length, frequency, damping, etc.) best match the ultrasonic properties of object 11.

Inasmuch as the present invention is subject to many variations, modifications and changes in detail, a number of which have been expressly stated herein, it is intended that all matter described throughout this entire specification or shown in the accompanying drawings be interpreted as illustrative and not in a limiting sense. It should thus be evident that a device constructed and method performed according to the concept of the present invention, and reasonably equivalent thereto, will accomplish the objects of the present invention and otherwise substantially improve the art of accurately and precisely positioning the focal point of an ultrasonic beam inside an object such as a pneumatic tire.

I claim:

1. An apparatus for the accurate positioning of an ultrasonic beam to nondestructively test an object, comprising:

ultrasonic transducer means for generating the ultrasonic beam and impinging the ultrasonic beam upon the object, the ultrasonic beam having a focal point and a beam axis; and, aiming means for generating a visible light beam having a focal point and a beam axis, said visible light beam axis coaxial with said ultrasonic beam axis and said ultrasonic, beam focal point and said visible light beam focal point aligned and thereafter selectively coaxially movable into and out of coincidence at points exterior and interior to the object.

2. An apparatus for the accurate positioning of an ultrasonic beam to nondestructively test an object, as set forth in claim 1, wherein said aiming means includes at least one high-intensity visible light point-source in fixed coaxial relation with said ultrasonic transducer means.

3. An apparatus for the accurate positioning of an ultrasonic beam to nondestructively test an object, as set forth in claim 2, wherein said aiming means further includes mirror means for focusing the light from said high-intensity visible light point-source at said visible light focal point, said mirror means in fixed coaxial relation with said ultrasonic transducer means.

4. An apparatus for the accurate positioning of an ultrasonic beam to nondestructively test an object, as set forth in claim 3, wherein the object is a tire, and said ultrasonic transducer means and said visible light beam aiming means are both immersed in a medium whose refractive index differs from that of air.

5. An apparatus for the accurate positioning of an ultrasonic beam to nondestructively test an object, as set forth in claim 1, wherein said aiming means includes a plurality of high-intensity visible light point-sources in fixed coaxial relation with said ultrasonic transducer means, the visible light from said plurality of high-intensity visible light point-sources directly impinging upon the surface of said object at said visible light beam focal point.

6. An apparatus for the accurate positioning of an ultrasonic beam to nondestructively test an object, as set forth in claim 5, wherein the object is a tire, and said ultrasonic transducer means and said visible light beam aiming means are both immersed in a medium whose refractive index differs from that of air.

7. A method for the accurate positioning of an ultrasonic beam to nondestructively test an object, comprising the steps of:
- generating an ultrasonic beam having a focal point and having a beam axis, and impinging the ultrasonic beam upon the object;
- generating a visible light beam having a focal point and having a beam axis coaxial with said ultrasonic beam axis, and impinging said visible light beam upon the object;
- aligning said ultrasonic beam focal point and said visible light beam focal point to coincide at an alignment spot; and,
- moving said aligned ultrasonic beam focal point to a point of interest within the object while maintaining said visible light beam focal point at said alignment spot.

8. A method for the accurate positioning of an ultrasonic beam to nondestructively test an object, as set forth in claim 7, further including the step of maintaining said visible light beam focal point at said alignment spot.

9. A method for the accurate positioning of an ultrasonic beam to nondestructively test an object, as set forth in claim 7, wherein said step of generating a visible light beam includes the steps of generating a point source of light and focusing said point source of light to said visible light beam focal point.

10. A method for the accurate positioning of an ultrasonic beam to nondestructively test an object, as set forth in claim 7, wherein said step of generating a visible light beam includes the steps of generating a plurality of substantially non-divergent light sources and directing said light sources to said visible light beam focal point.

11. A method for the accurate positioning of an ultrasonic beam to nondestructively test an object, as set forth in claim 7, wherein said step of aligning includes the steps of moving said visible light beam focal point to an alignment spot exterior to the object, and then moving said ultrasonic beam focal point to said alignment spot.

12. A method for the accurate positioning of an ultrasonic beam to nondestructively test an object, as set forth in claim 7, wherein said step of moving includes the step of moving said ultrasonic beam focal point to maximize the amplitude of ultrasonic energy reflected from said point of interest within the object.

13. A method for the accurate positioning of an ultrasonic beam to nondestructively test an object, as set forth in claim 12, further including the step of displaying the amplitude of the ultrasonic energy reflected by the object versus time.

* * * * *